(12) United States Patent
Ford

(10) Patent No.: US 6,846,282 B1
(45) Date of Patent: Jan. 25, 2005

(54) BRACHYTHERAPY APPARATUS AND METHODS

(75) Inventor: John C. Ford, Marietta, GA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 09/591,089

(22) Filed: Jun. 9, 2000

(51) Int. Cl.[7] .............................................. A61N 5/00
(52) U.S. Cl. ........................................................ 600/1
(58) Field of Search ............................ 600/1, 2, 3, 4, 600/5, 6, 7, 8, 427, 429, 439, 424; 606/130

(56) References Cited

U.S. PATENT DOCUMENTS

| | | | | |
|---|---|---|---|---|
| 5,339,812 A | * | 8/1994 | Hardy et al. ................. | 600/7 |
| 6,095,975 A | * | 8/2000 | Silvern ...................... | 600/439 |
| 6,129,670 A | * | 10/2000 | Burdette et al. ............ | 600/427 |
| 6,282,437 B1 | * | 8/2001 | Franck et al. ............... | 600/429 |
| 6,368,331 B1 | * | 4/2002 | Front et al. ................. | 606/130 |
| 2003/0065260 A1 | * | 4/2003 | Cheng et al. ............... | 600/427 |

* cited by examiner

Primary Examiner—Max F. Hindenburg
Assistant Examiner—Brian Szmal
(74) Attorney, Agent, or Firm—Beyer Weaver & Thomas LLP

(57) ABSTRACT

Brachytherapy is carried out with a needle to inject a radioactive seed into a patient's body. A space-fixed detector detects radiation from radiation emitters to determine the position of a deposited seed from the needle with reference to a space-fixed coordinate system. Markers may be affixed to the patient's body such that a body-fixed coordinate system can be determined in real time by an imaging device. Alternatively, earlier obtained patient's anatomical data may be referenced. After positions of earlier injected seeds are thus ascertained in real time in the body-fixed coordinate system, the stored anatomical data may be updated and a radiation dose distribution can be calculated from the determined seed positions. The calculated radiation dose distribution can be displayed and compared with a planned distribution.

54 Claims, 1 Drawing Sheet

US 6,846,282 B1

BRACHYTHERAPY APPARATUS AND METHODS

BACKGROUND OF THE INVENTION

This invention relates to apparatus for and methods in brachytherapy. More particularly, this invention relates to apparatus for and methods of accurately depositing radioactive seeds in a patient's body in a brachytherapy by calculating radiation dose distribution.

In the field of medicine, nuclear radiation may be used for diagnostic and therapeutic treatment of patients inflicted with cancer. Typically, more than half of these patients need radiation therapy either as a primary or as an adjunct mode of treatment. Conventional medical radiation sources used in these treatments include large fixed position machines such as linear accelerators as well as small, transportable radiation generating probes which provide a boost therapy. In the latter treatment system, a miniaturized probe capable of producing a high dose of radiation in a pre-defined geometry is inserted into a treatment volume. The treatment is commonly referred to as brachytherapy because the radiation source is located close to or, in some cases, within the treatment volume. Brachytherapy is advantageous in that high doses of ionizing radiation, measured in terms of energy/mass, are delivered to a localized volume of tissue such that the radiation is supplied primarily to the treatment volume without significantly affecting tissues in adjacent volumes. This ability, when combined with a rapid reduction in the radiation dose as a function of distance, shields distant anatomies from spurious radiation. Hence, the technique has provided excellent results for localized control of various tumors.

In applications where tumors under treatment are in the patient's prostate gland, an applicator such as a perineal template is commonly employed with one or more probes that contain seeds or radiation sources. The template has an array of openings for accepting a plurality of sequential tandem brachytherapy probes or needles. During operation, the template is positioned near tumors to be treated and referenced to one or more scanned images before the seeds are inserted into the openings.

During a brachytherapy operation, a physician needs to know exact positions of the seeds, as well as a radiation dosage distribution from these seeds. Additionally, it is desirable to quantify the radiation received by surrounding organs. Generally, locations and orientations of the needles are referenced to one or more images derived from modalities such as X-ray radiograph, computed tomography (CT), magnetic resonance (MR), ultrasound, or nuclear medicine scans of the patient.

Typically, for prostate cancer, images from a base to an apex of the prostate are obtained at 0.5 centimeter increments. Information on adjacent rectum, urethra and bladder is also captured. The information is correlated with the position of the applicator, which in turn is used as a reference for determining the needle position. The position of the seed inside the patient is determined relative to the needle and the template as a function of the needle length and orientation, minus a length of a remaining needle portion outside of the template.

The seed position determination process discussed above is laborious and is subject to operator errors and inaccuracies associated with the needle insertion. One source of error is the bending of the needle when it encounters a rigid anatomical portion. Another kind of error may be in the transformation of scanned image data to a coordinate system fixed to the patient's body. Yet another kind of error may be in the equipment calibration or usage.

In addition to the seed position data, information on the radiation dose distribution is also needed. If the radiation dose distribution at a target point is too low due to unforeseen conditions, the brachytherapy operation may be ineffective. If the radiation dose distribution at the target point is too high, the operation may have undesirable effects. Traditionally, the dose distribution analysis involves entering into a dosimetry computer the contours of the prostate, the urethra and the rectum target volume. Seed positions and seed strengths are then entered into the dosimetry computer. Based on the data entry, the dosimetry computer determines a dose distribution estimate. The data entry process is tedious and error-prone. Moreover, without a visual feedback, such dose distribution analysis is prone to accumulated errors. As noted above, furthermore, potential errors associated with the needle insertion process may affect the reliability of the seed position determining process.

SUMMARY OF THE INVENTION

It is therefore an object of this invention to provide apparatus for and methods in brachytherapy by which radioactive seeds can be accurately deposited in a patient's body by calculating dose distribution and displaying the calculated radiation dose distribution.

According to this invention, an injection device of a known type with a needle is used to inject a radioactive source (or the "seed") into a patient's body. The position of the injection device, hence that of the tip of its needle and that of the seed deposited therefrom, can be determined with reference to a space-fixed coordinate system by a space-fixed position detector. Markers are affixed to the patient's body such that a body-fixed coordinate system can be determined in real time by an imaging device. Alternatively, earlier obtained patient's anatomical data stored in a computer may be referenced. After positions of the seeds which have been injected are thus ascertained in real time with reference to a body-fixed coordinate system, the stored anatomical data may be updated and a radiation dose distribution can be calculated on the basis of the determined seed positions. The calculated radiation dose distribution can be displayed for a visual inspection and may be compared with a planned distribution such that the injection device can be robotically controlled to deposit the next seed at a desired position inside the patient's body for bringing about the planned distribution most effectively.

BRIEF DESCRIPTION OF THE DRAWINGS

The accompanying drawings, which are incorporated in and form a part of this specification, illustrate embodiments of the invention and, together with the description, serve to explain the principles of the invention. In the drawings.

DETAILED DESCRIPTION OF THE INVENTION

Figure 1:
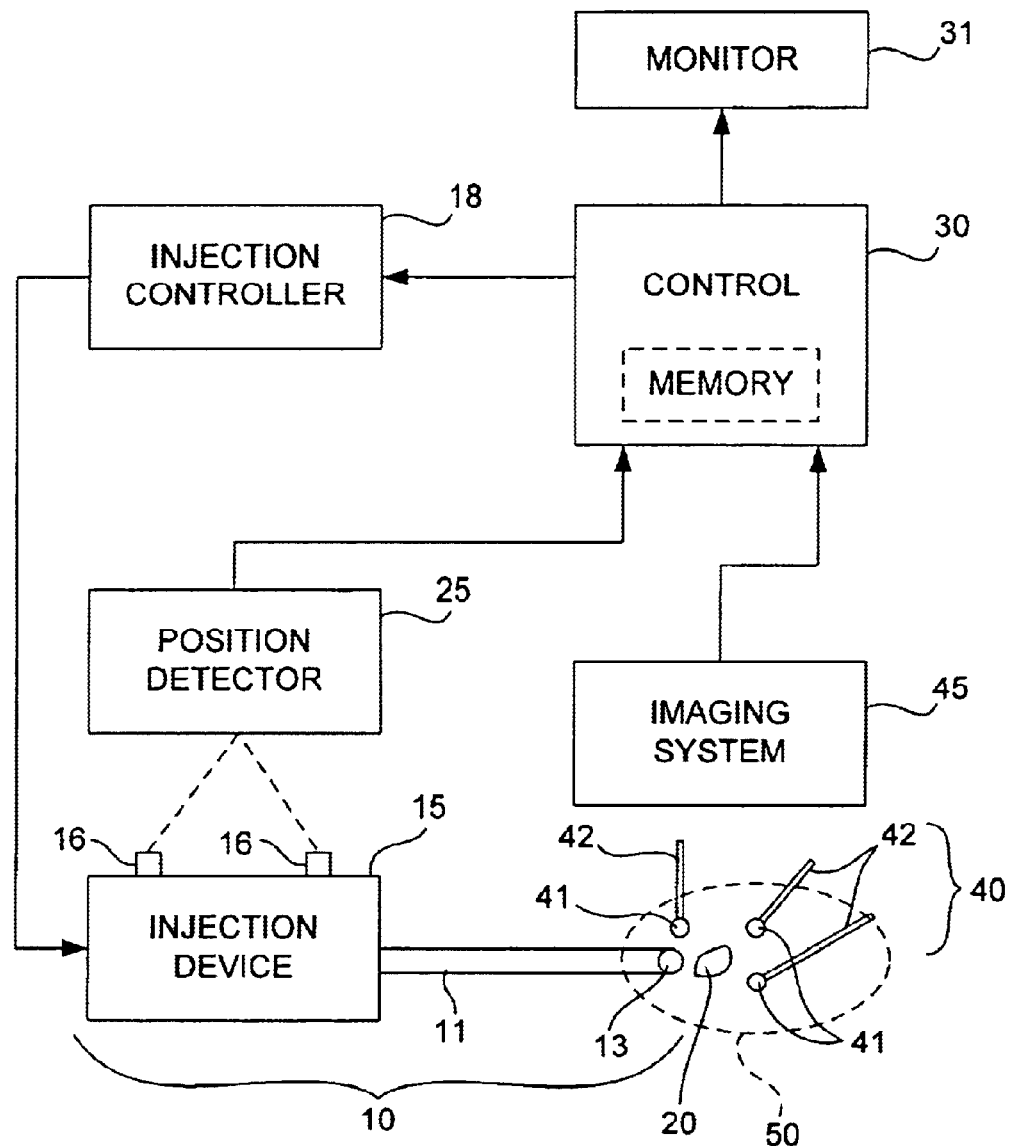
FIG. 1 is a schematic block diagram which shows both the basic structure of an apparatus and a brachytherapy method embodying this invention.

Since many methods and apparatus are included within the scope of this invention, the invention will be described in terms of its most basic principles common to all these methods and apparatus. With reference to FIG. 1, numeral 10 generally indicates an injector device for injecting a radioactive seed into a patient's body so as to be deposited at a selected target position. Such an injector device 10 may be generally described as having a needle 11 and a main body 15. The needle 11 is an injection needle of a known kind, being tubular with a longitudinally extending central passage (not shown) and having an opening 13 at its sharp tip through which a radioactive seed 20 is pushed out by means of a pusher (not shown) adapted to slide longitudinally through the interior of the central passage. The injector device 10 as a whole may be of a manually held kind, or alternatively adapted to be robotically operated.

Means for measuring and thereby determining the position and orientation of the injector device 10 may include a plurality of position-indicating units (or "position sources") 16 affixed to the exterior of the main body 15 of the injector device 10 for emitting or reflecting radiative energy and a position detector 25 affixed in space, that is, having a fixed position with reference to a space-fixed coordinate system. The radiative energy emitted or reflected by these position sources 16 may comprise ultrasonic waves or electromagnetic waves such as infrared radiation from an LED. Thus, the position detector 25 may be a camera system attached to the ceiling or a wall of the room in which the brachytherapy is to take place. The position data obtained by the position detector 25 by detecting the emitted or reflected radiation from the position-indicating units 16 are transmitted to and received by a control system 30 which may comprise a computer and serves to determine the position and orientation of the injector device 10 with respect to a space-fixed coordinate system. Since the shape and the dimensions of the injector device 10, inclusive of the length of its needle 11, are known, this means that the control system 30 can also determine the position of the opening 13 at the tip of the needle 11 with respect to this space-fixed coordinate system. If it is assumed that the radioactive seed 20 is deposited at the same position as that of the opening 13 of the needle 11, the position of the deposited seed 20 is also thus determined from the observed positions of the position-indicating units 16 on the main body 15 of the injector device 10.

What is important in brachytherapy, however, is not the positions of deposited seeds with reference to a space-fixed coordinate system but their positions with reference to the anatomical structure of the patient, or a body-fixed coordinate system affixed to the body of the patient. Such a body-fixed coordinate system may be defined by different methods or mixtures of methods.

One method of establishing such a body-fixed coordinate system is to implant markers, in a broad sense of the word and generally indicated by numeral 40, in a specified region 50 of the patient's body. According to one embodiment of the invention, position sources, as defined above, serving as the markers 40, may be affixed to the patient's body by any of the known techniques such that the radiation signals transmitted (by emission or reflection) therefrom can be detected by the same position detector 25 affixed to a space-fixed coordinate system as described above for the detection of the position-indicating units 16 on the main body 15 of the injector device 10. Such markers 40 for surface attachment may be provided with pins which will penetrate a bone lying near the surface of the patient's body for improved fixation.

According to another embodiment of the invention, a plurality of energy-transmitting position sources 41 are affixed to tips of as many needles 42 which are pre-positioned in the patient's body, surrounding a specified volume of interest as schematically shown in FIG. 1. These position sources 41 together can establish a body-fixed coordinate system. The positions of these needles can be determined by use of x-ray imaging, ultrasonic imaging, MRI, CT or other imaging techniques. Numeral 45 FIG. 1 generally indicates such an imaging system adapted, for example, to provide real time orthogonal x-ray images.

According to still another embodiment of the invention, the positions of the pre-positioned needles 42 are stored as "earlier obtained patient's anatomical data". For this purpose, a memory device for such data may be regarded as being included in the control system 30. As explained above, the positions of the markers 40 can be determined by real time imaging, but they can also be a part of such earlier obtained patient's anatomical data. Such earlier obtained data may be updated when the marker positions are detected in real time during a seed injection process as described above in order to more accurately represent the current anatomical conditions.

With a body-fixed coordinate system thus determined with reference to a space-fixed coordinate system, the position of each seed that is deposited through the injection needle 11 of the injector device 10 can be not only measured with reference to the space-fixed coordinate system but also determined with reference to a body-fixed coordinate system by the control system 30. A monitor 31 serves to display the calculated seed positions superposed to the marker positions or the earlier obtained patient's anatomical data The control system 30 further serves to carry out a dose distribution calculation for each radioactive seed deposited and to add it to the result of similar calculations for all earlier deposited seeds. The calculation may be carried out by using a known equation relating the dose rate with factors and parameters such as the air kerma strength which is a measure of how much energy is delivered at a given distance from the source, the dose rate constant which accounts for the type of radiation emitted, its energy, how much is absorbed in the covering of the seed, etc., a geometry factor which accounts for the variation of relative dose due to the spatial distribution of activity within the source, a radial dose function which accounts for the effects of absorption and scattering in the medium along the transverse axis of the seed, and an anisotropy factor which describes any anisotropy in the dose distribution as a function of angle about the source due to differences in self-filtration and scattering (See AAPM Radiation Therapy Committee Task Group 43, Med. Phys. 22:209 (1995)).

The results of the real-time dose calculation, carried out by the control system 30, may be displayed on the monitor 31 such that the user can visualize the build-up of the dose distribution as the seeds are implanted one by one. The calculated dose distribution thus obtained may be further compared with a planned distribution established preliminarily, serving as a part of a feedback loop by which it can be confirmed that a planned distribution is being achieved by the injection system. If the injector device 10 is of a robotically operated kind having an injector controller 18, as shown in FIG. 1, for automatically controlling the operation of the injector device 10, the control system 30 may be programmed so as to control the injection controller 18 according to the result of comparison between the dose distribution obtained in real time and the planned distribution such that the seed position at which the next seed to be injected from the injector device 10 should be deposited will be determined such that the planned distribution can best be approached and that the injector device 10 will be positioned and oriented accordingly so as to deposit the next seed at the selected position.

Such a mode of application is particularly useful in a situation where it is not possible to implant a seed at a certain position, or where errors have been accumulating in a pattern. If such a situation is detected on the monitor 31, the user can undertake alternative implantations and have the resultant dose distribution displayed.

It also goes without saying specifically that the user of the injector device 10 can have the position of the tip of its needle 11 displayed on the monitor 31 as the needle 11 is pushed through the patient's body, the real time image of the needle being superposed on the images of space-indicating markers in whatever form. This serves to improve the positioning of the needle 11 with respect to the target position where the seed is intended to be deposited.

According to a preferred embodiment of the invention, the control system 30 may allow, through its algorithm for calculating dose distribution, to determine hypothetical dose distributions and display them on the monitor 31 prior to having the "next" seed injected. These hypothetical distributions will be obtained by hypothetically selecting a kind of the seed and a position at which it is hypothetically deposited, and will serve to more effectively obtain the planned distribution.

Although the invention has been described above in most basic terms, many modifications and variations are possible within the scope of the invention, and the specification is intended to be interpreted broadly. Where the position-indicating units 16 affixed to the exterior of the main body 15 of the injector device 10 and the position sources 41 affixed to tips of the needles 42 were described as emitting or reflecting radiative energy, for example, the term "radiative energy" is intended to include not only electromagnetic waves in all wavelength ranges but also acoustic waves such as ultrasonic waves. Where they are reflectors, rather than emitters, of such radiative energy, a source therefor is intended to be provided, or otherwise available as a part of the apparatus. Similarly, the term "marker" is intended to include devices of all kinds which can be attached to and remain attached to a fixed position on or inside the patient's body and of which the position can be detected by a suitable detector.

The control system 30 is generally intended to comprise a computer and is intended to perform many functions. The functions to be performed by the control system 30 include analyzing the image data received from the position detector 25 and the imaging system 45 to determine positions with reference to a space-fixed coordinate system, transforming position data with reference to a space-fixed coordinate system into position data with reference to a body-fixed coordinate system, causing various data to be displayed on the monitor 31, serving as a memory device to store earlier obtained position data as well as planned dose distribution, and calculating a dose distribution from measured seed positions, as well as on the basis of a hypothetical seed additionally deposited.

In the claims section, some means-plus-function expressions are used for convenience. The "seed-position detecting means" includes the position-indicating units 16 (also referred to as the "energy-transmitting means") affixed to the injector device 10, the position detector 25 and the control system 30. The "real-time seed-position determining means" include the markers 40 generally, imaging system 45 and the control system 30. The "dosage calculating means" is represented by the control system 30. It is expected that the descriptions given above are sufficiently clear such that readers will have little or no trouble in identifying which of the described components are intended to effect the functions carried out by the different "means".

What is claimed is:

1. An apparatus for use with a human body for brachytherapy comprising:

an injection device having a hollow injection needle with an opening at a tip and seed-depositing means for having a radioactive seed pushed therethrough to be deposited in a patient's body through said opening proximal to said tip;

seed-position detecting means determining a position, with reference to a space-fixed coordinate system, of a seed deposited in the patient's body by said injection device;

real-time seed-position determining means determining a position of said deposited seed in real time with reference to a body-fixed coordinate system which is affixed to said patient's body, and dose calculating means calculating in real time a radiation dose distribution within a selected volume specified with respect to said body-fixed coordinate system due to seeds which have been deposited by said injection device.

2. The apparatus of claim 1 wherein said real-time position determining means includes:

memory means for storing earlier obtained patient's anatomical data; and coordinate-transforming means for identifying said body-fixed coordinate system with reference to said earlier obtained patient's anatomical data and determining position of said deposited seed with reference to said body-fixed coordinate system from the position of said seed with respect to said space-fixed coordinate system determined by said seed-position detecting means.

3. The apparatus of claim 1 wherein said dose calculating means calculates a hypothetical radiation dose distribution by assuming that a seed has been hypothetically deposited at a hypothetically selected position in said patient's body.

4. The apparatus of claim 1 further comprising injector controlling means for making a comparison between said calculated radiation dose distribution and a predetermined distribution plan, determining a next seed position where a next seed should be deposited in said patient's body according to result of said comparison and controlling said injection device according to said determined next position.

5. The apparatus of claim 1 further comprising display means for providing in real time a visual display of said injection needle with reference to said body-fixed coordinate system as said injection needle is moved through said patient's body.

6. The apparatus of claim 1 further comprising reference point detecting means for detecting in real time reference point position data with respect to said space-fixed coordinate system on positions of at least portions of markers affixed to selected parts of said body, and a display means for providing in real time a visual display of said reference point position data and the positions of deposited seeds.

7. An apparatus for use with a human body for brachytherapy comprising:

an injection device having a hollow injection needle with an opening at a tip and seed-depositing means for having a radioactive seed pushed therethrough to be deposited in a patient's body through said opening proximal to said tip;

seed-position detecting means determining a position, with reference to a space-fixed coordinate system, of a seed deposited in the patient's body by said injection device;

real-time seed-position determining means determining a position of said deposited seed in real time with reference to a body-fixed coordinate system which is affixed to said patient's body; and dose calculating means calculating in real time a radiation dose distribution within a selected volume specified with respect to said body-fixed coordinate system due to seeds which have been deposited by said injection device;

wherein said seed-position detecting means include:

energy transmitting means attached to said injection device for causing energy to be transmitted therefrom;

a detector at a fixed position with respect to said space-fixed coordinate system for receiving said energy propagated from said energy propagating means; and means for determining position and orientation of said injection device based on the energy propagated from said energy propagating means and received by said detector and thereby determining position of said deposited seed from the position of said opening at said tip of said injection needle.

8. An apparatus for use with a human body for brachytherapy comprising:

an injection device having a hollow injection needle with an opening at a tip and seed-depositing means for having a radioactive seed pushed therethrough to be deposited in a patient's body through said opening proximal to said tip;

seed-position detecting means determining a position, with reference to a space-fixed coordinate system, of a seed deposited in the patient's body by said injection device;

real-time seed-position determining means determining a position of said deposited seed in real time with reference to a body-fixed coordinate system which is affixed to said patient's body; and dose calculating means calculating in real time a radiation dose distribution within a selected volume specified with respect to said body-fixed coordinate system due to seeds which have been deposited by said injection device;

wherein said real-time seed-position determining means include:

markers affixed to selected parts of said body for defining said body-fixed coordinate system;

reference point detecting means for detecting in real time reference point position data with respect to said space-fixed coordinate system on positions of at least portions of said markers; and reference means determining a position of said deposited seed with reference to said body-fixed coordinate system from the position of said seed determined by said seed-position detecting means and the reference point position data detected by said reference point detecting means.

9. The apparatus of claim 8 wherein at least one of said markers comprises a needle with a front end and a back end and inserted in said patient's body, a front end being attached to a radiation transmitting means for transmitting a position-indicating signal for indicating the position of said front end, said back end being positioned outside of said patient's body so as to be observable by said seed-position detecting means.

10. The apparatus of claim 8 further comprising display means for providing in real time a visual display of said reference point position data and the positions of deposited seeds.

11. The apparatus of claim 8 further comprising memory means for storing earlier obtained patient's anatomical data; and updating means for updating said earlier obtained patient's anatomical data by said reference point position data detected by said reference point detecting means.

12. An apparatus for use with a human body for brachytherapy comprising:

an injection device having a hollow injection needle with an opening at a tip and seed-depositing means for having a radioactive seed pushed therethrough to be deposited in a patient's body through said opening proximal to said tip;

seed-position detecting means determining a position, with reference to a space-fixed coordinate system, of a seed deposited in the patient's body by said injection device;

real-time seed-position determining means determining a position of said deposited seed in real time with reference to a body-fixed coordinate system which is affixed to said patient's body;

dose calculating means calculating in real time a radiation dose distribution within a selected volume specified with respect to said body-fixed coordinate system due to seeds which have been deposited by said injection device; and display means providing in real time a visual display of earlier obtained patient's anatomical data and the positions of deposited seeds;

wherein said real-time position determining means includes:

memory means for storing said earlier obtained patient's anatomical data; and coordinate-transforming means for identifying said body-fixed coordinate system with reference to said earlier obtained patient's anatomical data and determining position of said deposited seed with reference to said body-fixed coordinate system from the position of said seed with respect to said space-fixed coordinate system determined by said seed-position detecting means.

13. A method in brachytherapy comprising the steps of:

depositing a radioactive seed in a patient's body through an opening at a needle tip of an injection device;

determining space-position of said deposited seed with reference to a space-fixed coordinate system;

determining body-position of said deposited seed in real time with reference to a body-fixed coordinate system which is affixed to said patient's body; and calculating in real time a radiation dose distribution within a selected volume specified with respect to said body-fixed coordinate system due to seeds which have been deposited by said injection device.

14. The method of claim 13 wherein the step of determining said body-position of said deposited seed includes the steps of:

affixing markers to selected parts of said patient's body;

detecting said markers in real time by a detector which is affixed at a fixed position with reference to said space-fixed coordinate system; and determining said body-position of said deposited seed from the detected positions of said markers and said determined space-position of said deposited seed.

15. The method of claim 14 wherein at least one of said markers comprises a needle with a front end and a back end, said front end being attached to a radiation transmitting means for transmitting a position-indicating signal, said back end being outside of said patient's body, said position-indicating signal being detected by a space-fixed signal detector.

16. The method of claim 14 further comprising the step of displaying in real time the positions of said markers and positions of seeds which have been deposited by said injection device.

17. The method of claim 14 further comprising the steps of updating earlier obtained anatomical data on said patient's body by using the positions of said detected markers.

18. The method of claim 13 wherein the step of determining said body-position of said deposited seed includes the steps of:

retrieving earlier obtained anatomical data on said patient's body;

determining said body-fixed coordinate system from said earlier obtained anatomical data; and determining said body-position of said deposited seed from body-fixed coordinate system and said determined space-position of said deposited seed.

19. The method of claim 18 further comprising the step of displaying in real time said earlier obtained anatomical data on said patient's body and positions of seeds which have been deposited by said injection device.

20. The method of claim 13 further comprising the steps of calculating hypothetical dose distribution by assuming that a seed has been hypothetically deposited at selected positions inside said patient's body and causing said calculated hypothetical dose distributions to be displayed.

21. The method of claim 13 further comprising the steps of:

making a comparison between said calculated radiation dose distribution and a predetermined distribution plan;

determining a next seed position where a next seed should be deposited in said patient's body according to result of said comparison; and controlling said injection device according to said determined next position to inject a next seed at said determined next seed position.

22. The method of claim 13 further comprising the step of displaying an image of said injection needle in real time with reference to said body-fixed coordinate system as said injection needle is pushed through said patient's body.

23. A method in brachytherapy comprising the steps of:

depositing a radioactive seed in a patient's body through an opening at a needle tip of an injection device;

determining space-position of said deposited seed with reference to a space-fixed coordinate system;

determining body-position of said deposited seed in real time with reference to a body-fixed coordinate system which is affixed to said patient's body, and calculating in real time a radiation dose distribution within a selected volume specified with respect to said body-fixed coordinate system due to seeds which have been deposited by said injection device;

wherein the step of determining space-position of said deposited seed includes the steps of:

causing energy to be propagated from fixed positions on said injection device;

detecting said propagated energy by a detector at a fixed position with respect to said space-fixed coordinate system; and assuming that said deposited seed is located where said opening at said needle tip of said injection device was when said seed was deposited.

24. An apparatus for brachytherapy, comprising:

a seed delivery device comprising a position-indicating unit;

a position detector configured to sense said position-indicating unit; and a computer coupled to said position detector, said computer configured to determine a position of a seed within a patient body with reference to a space-fixed coordinate system based on a position of said position-indicating unit, and a radiation dose distribution relative to a body-fixed coordinate system based at least on said position of said seed.

25. The apparatus of claim 24, wherein said seed has been deposited by said seed delivery device.

26. The apparatus of claim 24, wherein said seed is being carried by said seed delivery device.

27. The apparatus of claim 24, wherein said position-indicating unit emits or reflects radiative energy.

28. The apparatus of claim 27, wherein said radiative energy comprises ultrasonic energy or electromagnetic energy.

29. The apparatus of claim 24, wherein said position detector comprises a camera.

30. The apparatus of claim 24, further comprising a screen coupled to said computer.

31. The apparatus of claim 30, wherein said screen provides a visual display of said seed delivery device with reference to said body-fixed coordinate system.

32. The apparatus of claim 30, wherein said screen provides a visual display of said deposited seed.

33. A method in brachytherapy, comprising:

placing a radioactive seed in a patient's body via a delivery device;

determining a position of said seed with reference to a space-fixed coordinate system;

determining a body-fixed coordinate system based on markers within said patient's body; and calculating a radiation dose distribution relative to said body-fixed coordinate system due to said seed.

34. The method of claim 33, further comprising releasing said seed from said delivery device.

35. The method of claim 33, wherein said determining a position of said seed comprises sensing a position-indicating unit carried on said delivery device.

36. The method of claim 35, wherein said sensing comprises detecting radiative energy emitted or reflected by said position-indicating unit.

37. The method of claim 36, wherein said radiative energy comprises ultrasonic energy or electromagnetic energy.

38. The method of claim 35, wherein said sensing is performed using a camera.

39. The method of claim 33, wherein said determining a body-fixed coordinate system comprises determining positions of said markers.

40. The method of claim 39, wherein said determining positions of said markers comprises using an X-ray imaging system, an ultrasonic imaging system, a MRI system, or a CT system.

41. The method of claim 33, further comprising displaying said delivery device with reference to said body-fixed coordinate system on a screen.

42. An apparatus for brachytherapy, comprising:

a seed delivery device comprising a position-indicating unit;

a position detector configured to sense said position-indicating unit;

an imaging system configured to sense markers within a patient body; and a computer coupled to said position detector and said imaging system, said computer configured to determine a position of a seed with reference to a space-fixed coordinate system based on a position of said position-indicating unit, a body-fixed coordinate system based on positions of said markers, and a radiation dose distribution relative to said body-fixed coordinate system based at least on said position of said seed with reference to said space-fixed coordinate system.

43. The apparatus of claim 42, wherein said seed has been deposited by said seed delivery device.

44. The apparatus of claim 42, wherein said seed is being carried by said seed delivery device.

45. The apparatus of claim 42, wherein said position-indicating unit emits or reflects radiative energy.

46. The apparatus of claim 45, wherein said radiative energy comprises ultrasonic energy or electromagnetic energy.

47. The apparatus of claim 42, wherein said position detector comprises a camera.

48. The apparatus of claim 42, wherein said markers comprise pins.

49. The apparatus of claim 48, wherein said markers comprise energy-transmitting position sources.

50. The apparatus of claim 42, wherein said imaging system comprises an X-ray imaging system, an ultrasonic imaging system, a MRI system, or a CT system.

51. The apparatus of claim 42, further comprising a screen coupled to said computer.

52. The apparatus of claim 51, wherein said screen provides a visual display of said seed delivery device with reference to said body-fixed coordinate system.

53. An apparatus for brachytherapy, comprising:

a seed delivery device comprising a position-indicating unit;

a position detector configured to sense said position-indicating unit;

markers within a patient body;

an imaging system configured to sense said markers; and a computer coupled to said position detector and said imaging system, said computer configured to determine a position of a seed with reference to a space-fixed coordinate system based on a position of said position-indicating unit, a body-fixed coordinate system based on positions of said markers, and a radiation dose distribution relative to said body-fixed coordinate system based at least on said position of said seed with reference to said space-fixed coordinate system.

54. An apparatus for use with a human body for brachytherapy comprising:

an injection device having a hollow injection needle with an opening at a tip and seed-depositing means for having a radioactive seed pushed therethrough to be deposited in a patient's body through said opening proximal to said tip;

seed-position detecting means determining a position, with reference to a space-fixed coordinate system, of a seed deposited in the patient's body by said injection device;

real-time seed-position determining means determining a position of said deposited seed in real time with reference to a body-fixed coordinate system which is affixed to said patient's body;

dose calculating means calculating in real time a radiation dose distribution within a selected volume specified with respect to said body-fixed coordinate system due to seeds which have been deposited by said injection device; and display means providing in real time a visual display of earlier obtained patient's anatomical data and the positions of deposited seeds.

* * * * *